United States Patent [19]

Vasconcellos et al.

[11] Patent Number: 4,907,591

[45] Date of Patent: Mar. 13, 1990

[54] SURGICAL INSTRUMENT FOR ESTABLISHING COMPRESSION ANASTOMOSIS

[75] Inventors: Alfred V. Vasconcellos, Cranston, RI; Ionel E. Teodorescu, Woodside, N.Y.; Joel W. Cummings, Beckley, MA.; Dean E. McBeth, Groton-on-Hudson, N.Y.

[73] Assignee: Pfizer Hospital Products Group, Inc., New York, N.Y.

[21] Appl. No.: 174,570

[22] Filed: Mar. 29, 1988

[51] Int. Cl.$^4$ ............................................. A61B 17/04
[52] U.S. Cl. ..................................... 606/154; 606/171
[58] Field of Search ................... 128/334 R, 335, 305; 227/19, DIG. 1

[56] References Cited

U.S. PATENT DOCUMENTS

| | | | |
|---|---|---|---|
| D. 271,994 | 12/1983 | Noiles et al. | D24/26 |
| D. 273,041 | 3/1984 | Noiles et al. | D24/26 |
| 4,289,133 | 9/1981 | Rothfuss | 128/334 C |
| 4,304,236 | 12/1981 | Conta et al. | 128/325 |
| 4,319,576 | 3/1982 | Rothfuss | 128/305 |
| 4,351,466 | 9/1982 | Noiles | 227/8 |
| 4,423,730 | 1/1984 | Gabbay | 128/334 R |
| 4,473,077 | 9/1984 | Noiles et al. | 128/305 |
| 4,476,863 | 10/1984 | Kanshin et al. | 128/305 |
| 4,485,817 | 12/1984 | Swiggett | 128/334 R |
| 4,488,523 | 12/1984 | Shichman | 128/334 R |
| 4,573,468 | 3/1986 | Conta et al. | 128/305 |
| 4,576,167 | 3/1986 | Noiles | 128/334 R |
| 4,598,712 | 7/1986 | Rebuffat et al. | 128/334 C |
| 4,603,693 | 8/1986 | Conta et al. | 128/305 |
| 4,606,343 | 8/1986 | Conta et al. | 128/305 |
| 4,646,745 | 3/1987 | Noiles | 128/334 R |
| 4,667,673 | 5/1987 | Li | 128/334 C |
| 4,681,108 | 7/1987 | Rosati et al. | 128/334 R |
| 4,703,887 | 11/1987 | Clanton et al. | 227/19 |
| 4,728,020 | 3/1988 | Green et al. | 227/19 |
| 4,754,909 | 7/1988 | Barker et al. | 227/19 |
| 4,776,506 | 10/1988 | Green | 227/19 |

Primary Examiner—Edward M. Coven
Assistant Examiner—Gary Jackson
Attorney, Agent, or Firm—Peter C. Richardson; Lawrence C. Akers; John L. LaPierre

[57] ABSTRACT

A surgical instrument for installing a plurality of interlocking coupling members forming a compression anastomosis assembly, particularly suitable for use in achieving anastomosis of a resected tubular organ, with the instrument having a cutting portion designed and configured for rotational movement as the cutter advances to perform its intended functions of severing tissue and at least a portion of one of the members of the assembly. Also disclosed is a dual locking feature for alternately locking a driving component and an aligning component against movement where, in a first mode, the aligning component is operative when the driving component is locked and, in a second mode, the driving component is operative when the aligning component is locked. Additionally disclosed is a unique aligning component for aligning and exerting a compressive force on members of an associated coupling assembly. Lastly, there is disclosed a surgical instrument capable of assuming a variety of configurations to accommodate a number of anatomical orientations and operating situations.

31 Claims, 11 Drawing Sheets

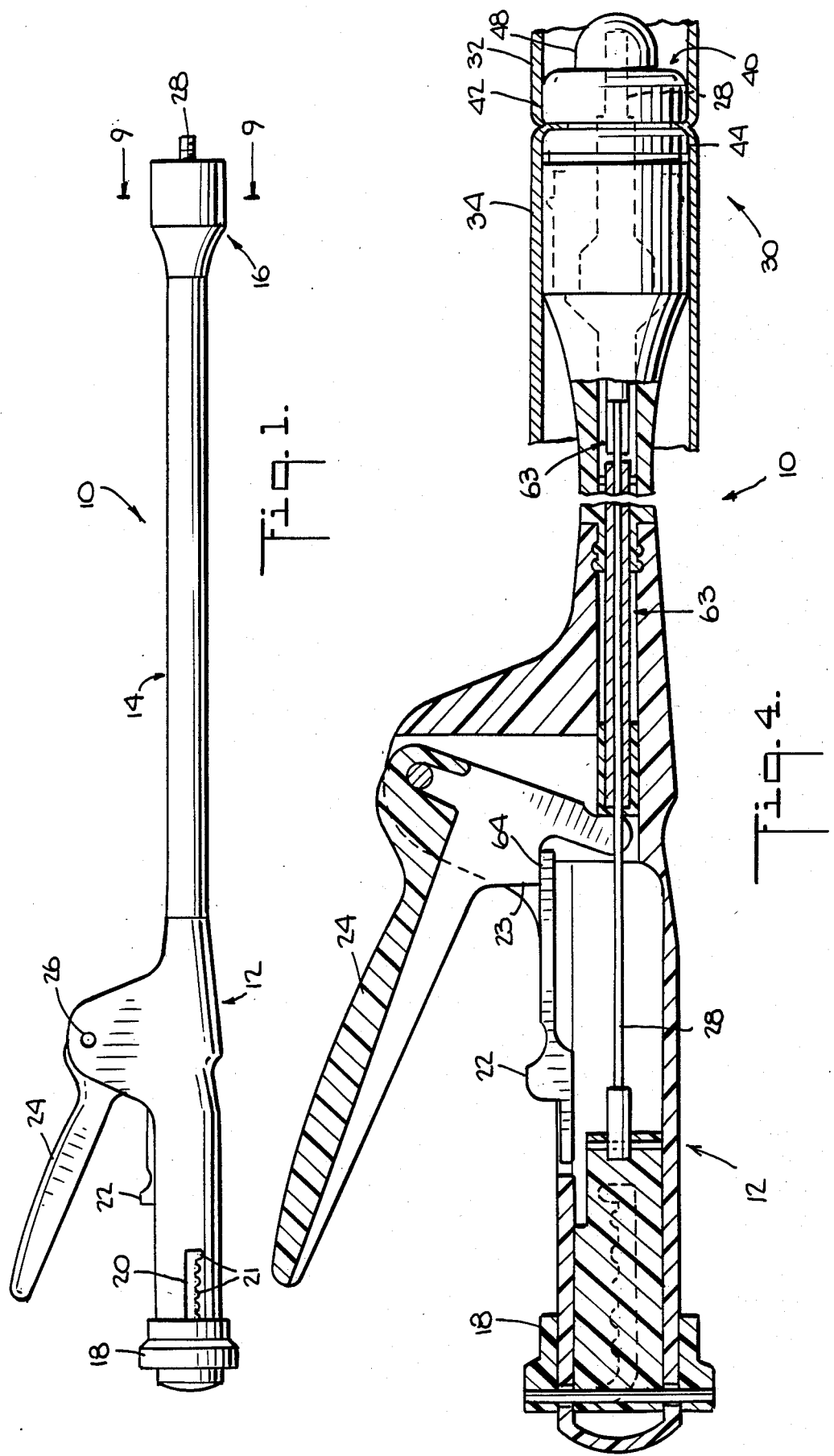

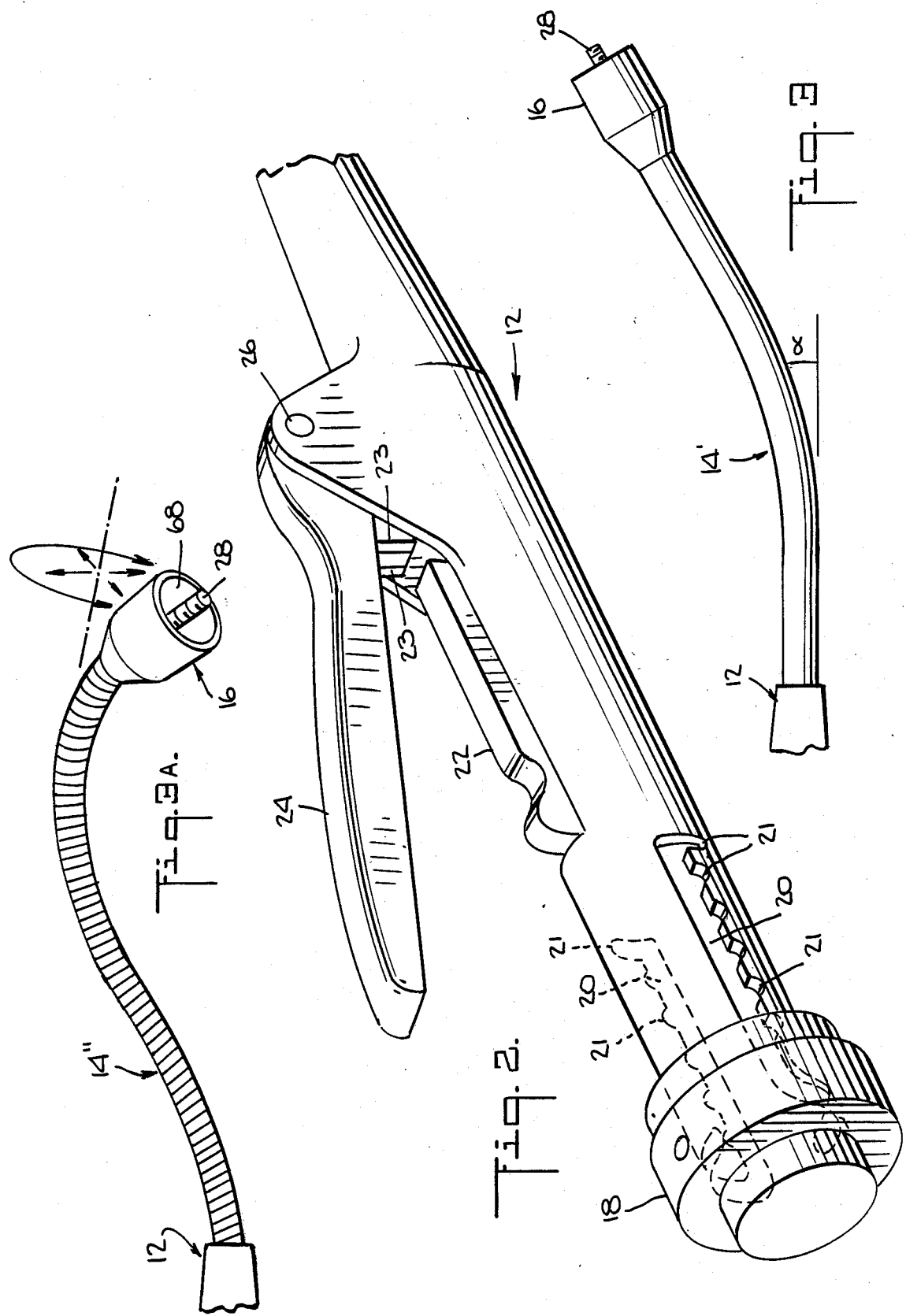

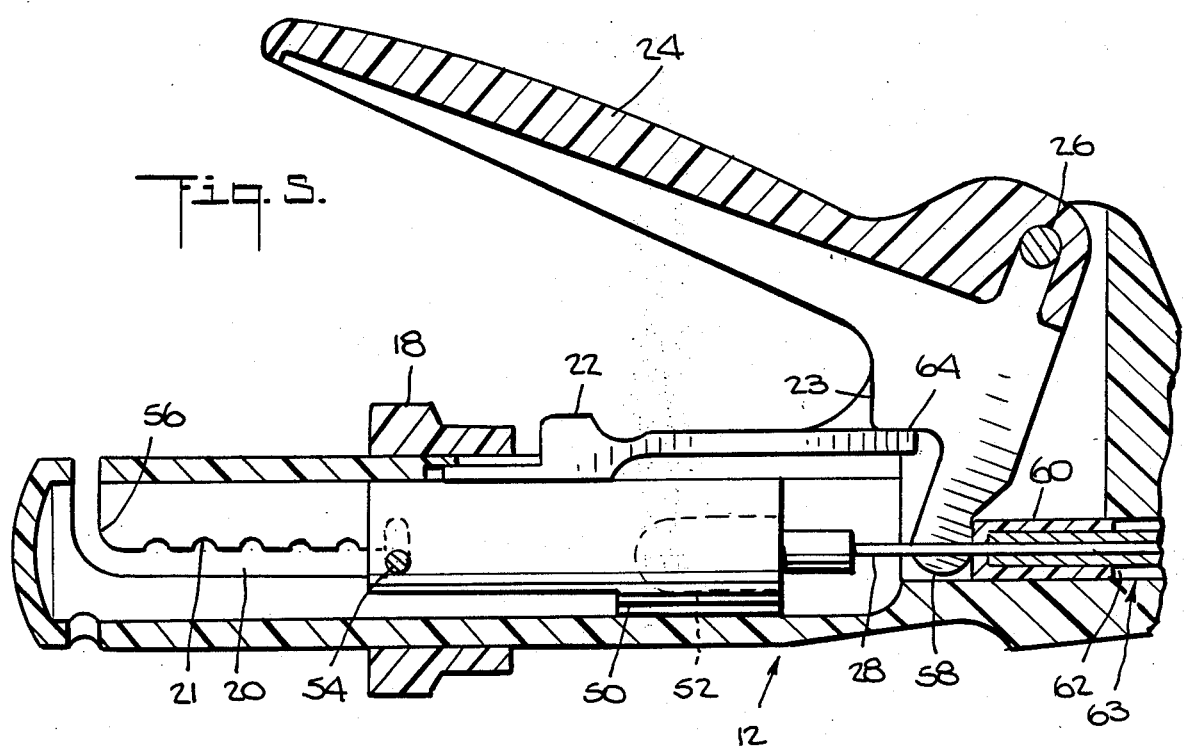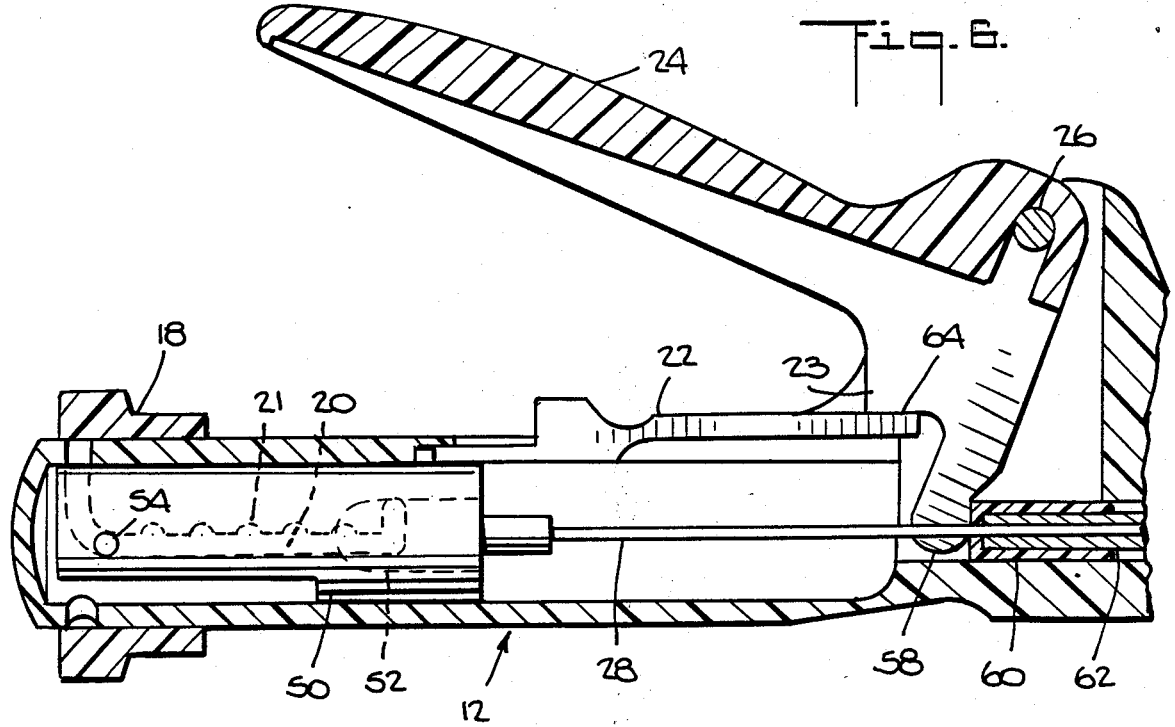

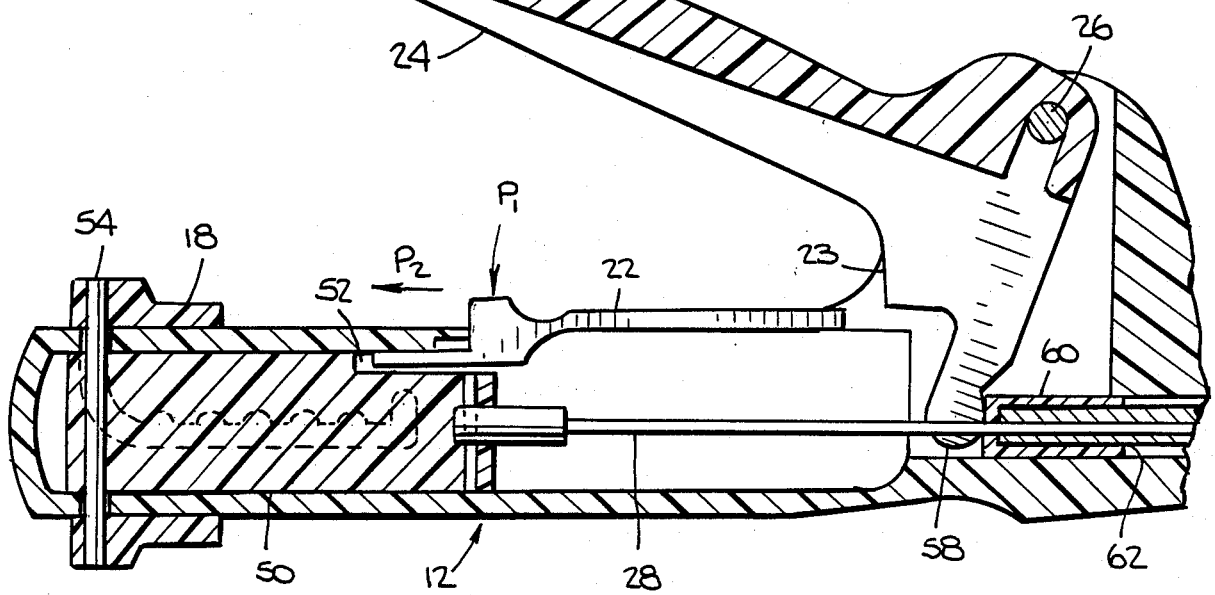
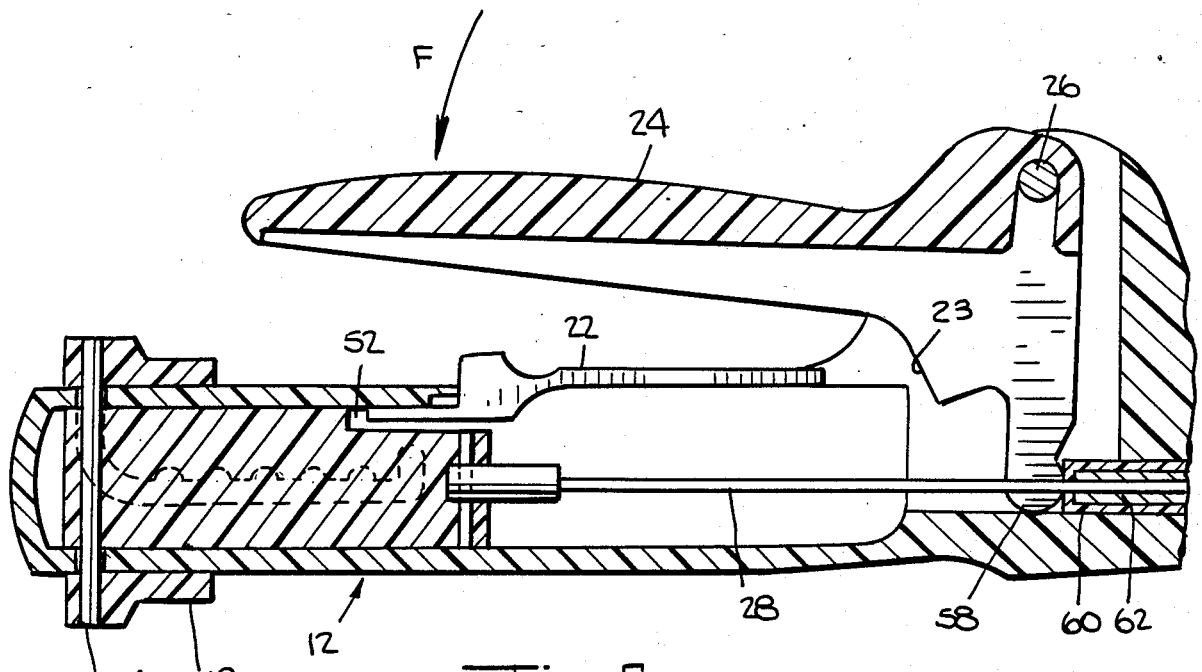

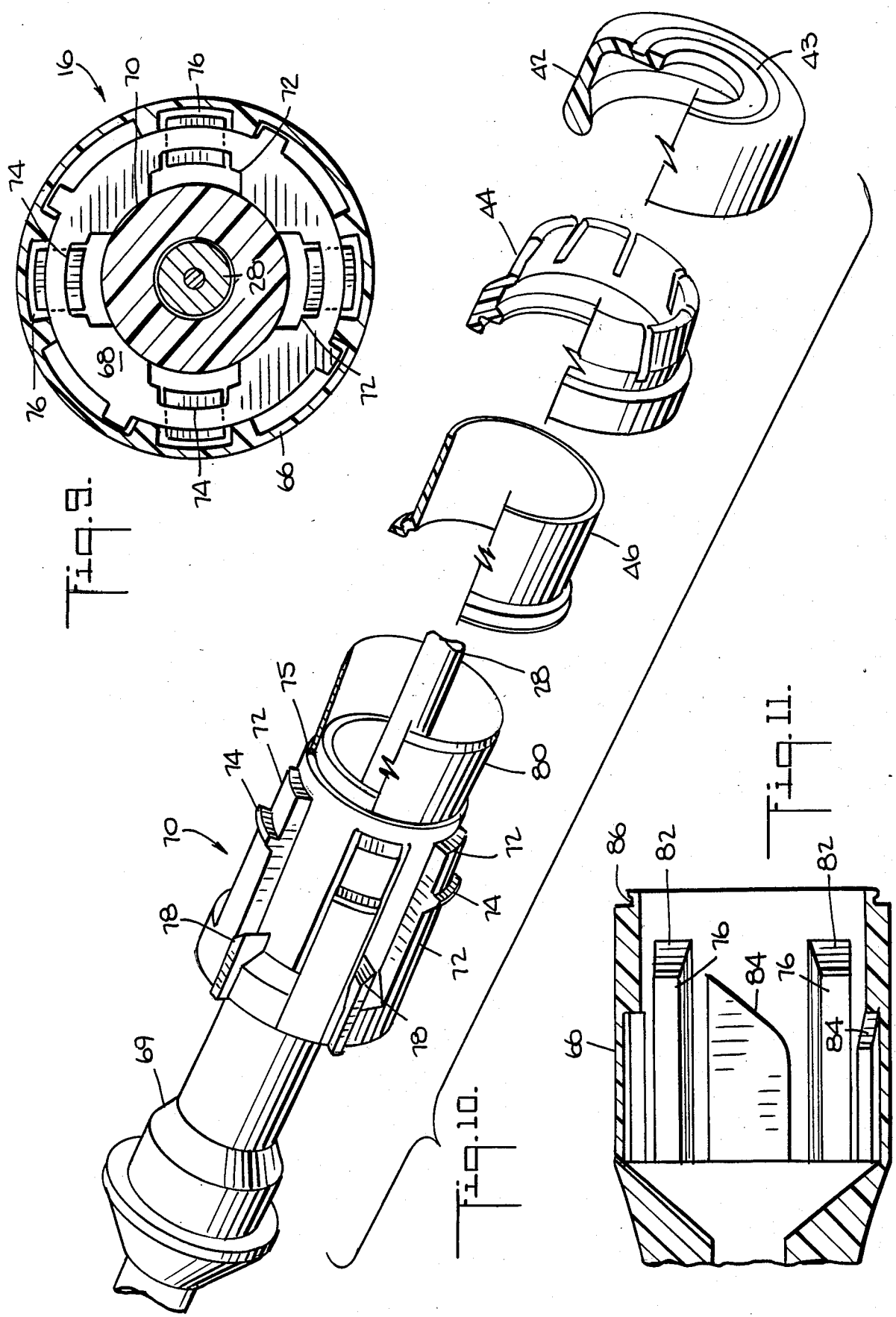

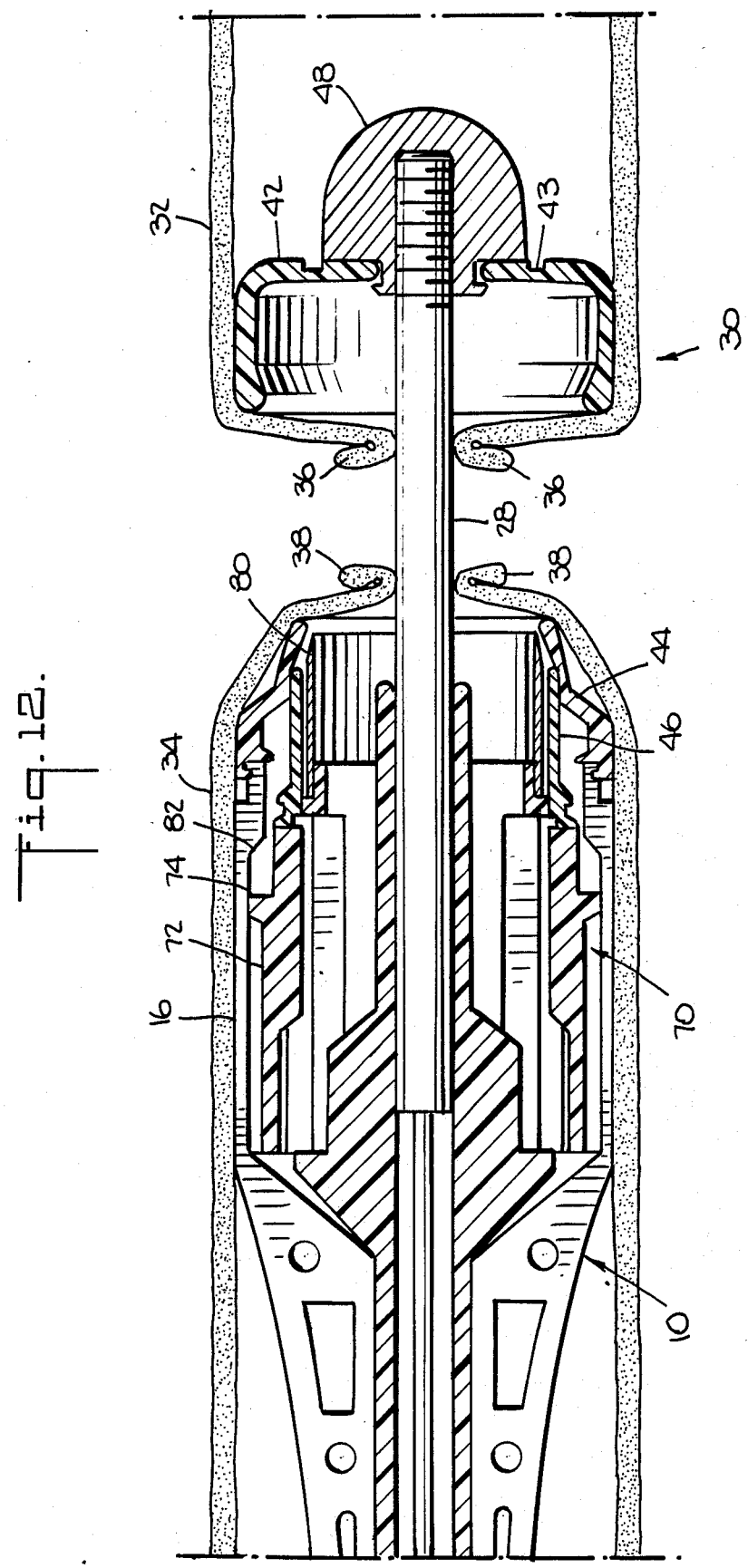

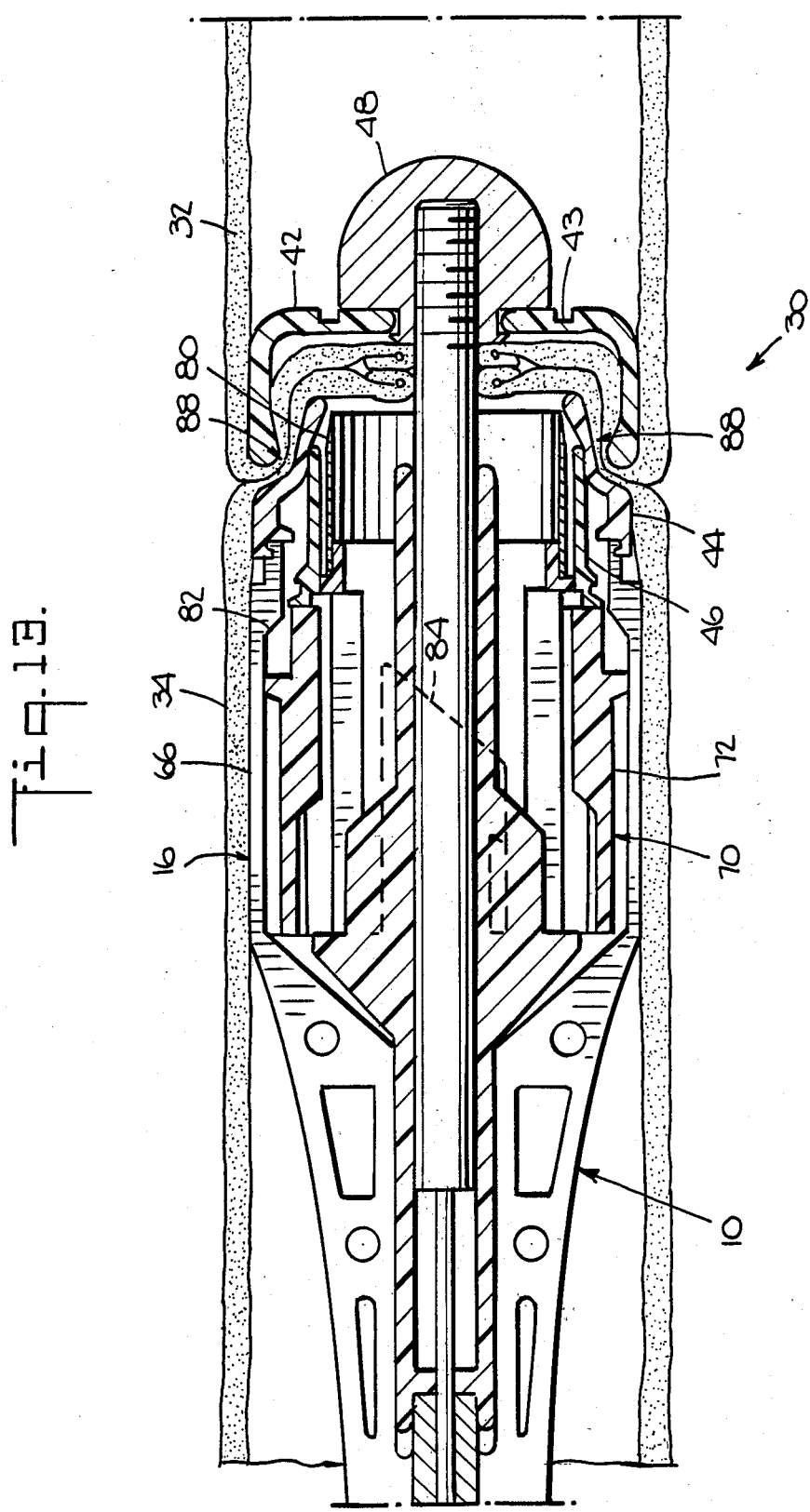

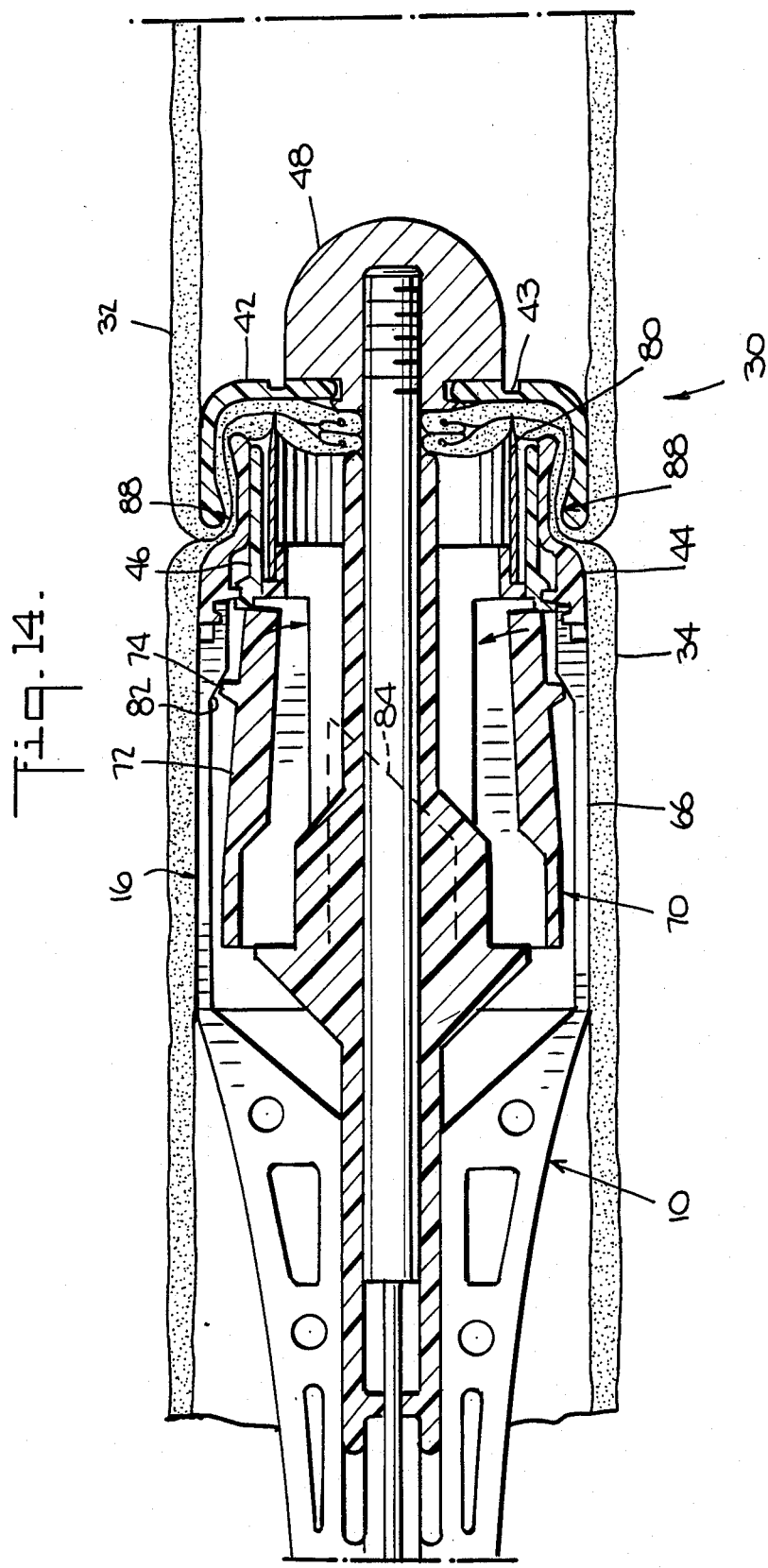

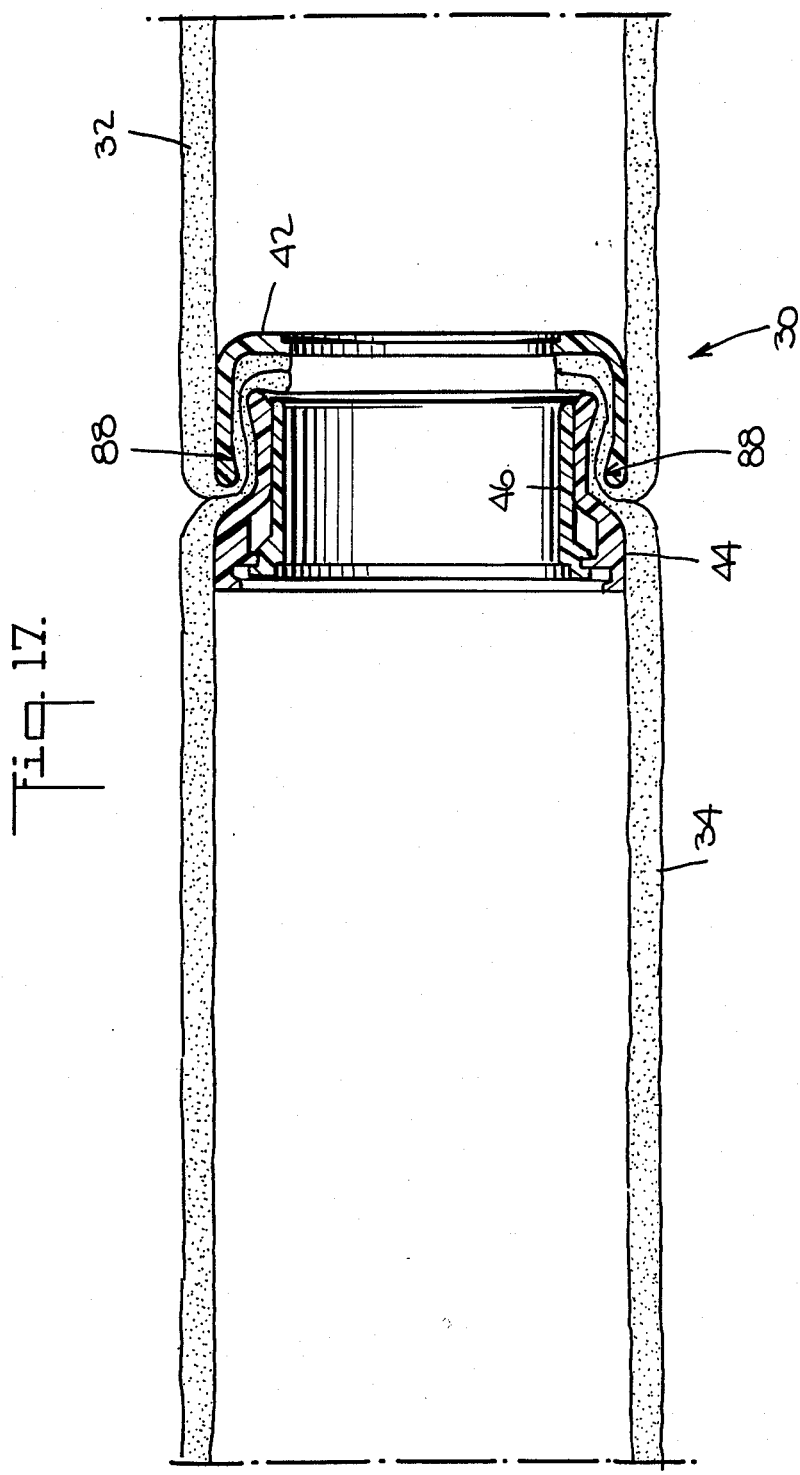

SURGICAL INSTRUMENT FOR ESTABLISHING COMPRESSION ANASTOMOSIS

BACKGROUND OF THE INVENTION

The present invention generally relates to an anastomosis of living tissue and, more particularly, it relates to a surgical instrument particularly adapted for use in the installation of an assembly of interlocking coupling members to achieve compression anastomosis of tubular structures. The instrument, developed to facilitate placement of the coupling assembly in a patient and to enhance in the removal of the instrument after placement, includes a novel cutting element which incorporates a rotary motion as the cutter advances through tissue and the coupling assembly. Additionally, the instrument might include a unique locking feature to improve operational safety, a unique coupling member aligning feature to enhance both in positioning of the coupling members and in applying compressive force to the members, and a unique flexible portion to accommodate a variety of surgical conditions.

A compression anastomosis coupling assembly is typically used when a segment of colon, or like tubular organ, is to be resected. After a section of the colon is removed, leaving opposed, proximal and distal, free ends, coaxially oriented coupling members are introduced, aligned and brought into locking engagement. The coupled members capture and compress the free ends of the colon together to effect an anastomosis by holding tissue in compression until healing occurs. Blood supply to the captured tissue is restricted. Necrosis takes place in the area of the colon captured within the assembly without causing excessive inflammation and trauma. Thereafter, the coupled assembly detaches from the anastomotic site and is expelled spontaneously through the rectum. After assembly expulsion, the colon provides an open passageway at the anastomotic site substantially as that which existed before resectioning.

Disclosure of a known type of surgical instrument used to install an assembly for circular anastomosis of hollow organs can be found in U.S. Pat. No. 4,681,108. This device advanced the then known art field by introducing a circular mechanical anastomotic gun suitable for performing circular anastomosis in hollow organs using a compressive device. Previously, in the majority of cases, a mechanical gun had been used in systems incorporating a number of metallic staples which were driven into tissue edges to achieve the anastomosis. Specifically, the device disclosed in the aforementioned patent includes three coaxial tubular elements, means for carrying and means for positioning members of a coupling assembly, a circular cutting blade, and a driving means for first advancing the coupling members into engagement and then advancing the circular blade for cutting. The new surgical instrument herein disclosed further advances the art field by introducing a cutter which rotates as its advances. The rotational movement of the cutter has the advantages of reducing the cutting force necessary to cut through both captured excess organ tissue and a coupling member of the assembly to provide an open passageway for material passage therethrough. The existing patented instrument includes a threaded knob which is rotated for positioning the outer coupling element and for exerting a compressive force between the outer and intermediate coupling elements prior to full locking assembly of the coupling elements.

The present device enhances coupling member positioning by providing a sliding-approximation system for easier and quicker operation. Also, the present device might feature an automatic locking system for securing one of the coupling members in a variety of positions relative to the other coupling members as a further refinement of the sliding approximation system. Furthermore, the sliding approximation system is designed and configured to provide an increased mechanical advantage thus reducing the necessary force applied by the user to achieve compression between assembly coupling members. An additional feature of the new instrument which is an improvement over known devices relates to an improved safety locking system which provides for alternately locking the instrument aligning and driving features. Specifically, the locking feature allows for either aligning or driving at a given instant but not simultaneously, namely, when the aligning feature is operational the driving feature is inoperative and, conversely, when the driving feature is operational the aligning feature is inoperative. Also, the new instrument might be either disposable or reusable. Furthermore, the instrument might include an anatomically curved segment for ease in introducing the device into a patient. Lastly, an improvement not known in the art is that the instrument might be sufficiently flexible to accommodate a variety of anatomical orientations and operating conditions.

The primary objective of the present invention is to further advance the art field by providing a surgical instrument which is used to establish compression anastomosis in tubular organs and which is an improvement over existing devices. Accordingly, herein disclosed is a surgical instrument which is especially designed and configured for greater ease in installation of a compression anastomosis coupling assembly and which incorporates a rotary cutting device. Furthermore, the instrument might incorporate unique locking, aligning and orienting features for enhanced device safety and operation.

SUMMARY OF THE INVENTION

The device of the present invention is a novel surgical instrument designed and configured for installing a coupling assembly, having a plurality of coupling members, to establish compression anastomosis in a tubular organ. The instrument comprises a body having a bore and includes a driver, a cutter, and means for supporting coupling members of the assembly. The instrument additionally includes means for imparting rotational movement to the cutter, means for aligning the coupling members and means for driving the driver to urge the coupling members into locking engagement and advancing and rotating the cutter. The driving means might include a conduit slidably disposed in the bore with the first end of the conduit being adapted to engage a lever and a second end of the conduit being adapted to engage the driver means. Preferably the instrument comprises a handle portion, an intermediate portion and a head portion, with the head portion having a recess intersecting the bore and the recess including therein the driver and the cutter. The recess is dimensioned and configured to provide means for guiding the movement of the driver and means for imparting rotational movement to the cutter. Rotary movement of the cutter can be achieved by providing a ram engaging a complementary projection wherein the projection, provided either on the driver or in the recess, glides along a coacting ramp surface. The intermediate portion of the instrument can either be straight or curved, with a curvature ranging from about 10° to about 25° and a preferred curvature being about 15°.

In one form of the invention, contemplated to be within the scope of the disclosure, the surgical instrument includes one or more locking means for alternately locking the driving means and the aligning means against movement. A locking device is adapted for movement between two locking positions. In a first location, the driving means is locked and the aligning means is operational whereas, in a second location, the aligning means is locked and the driving means is operational. Both the driving means and the aligning means are not simultaneously operative.

In another contemplated form of the invention, the surgical instrument includes an aligning means comprising a core having a first end coupled to one of the coupling members of the assembly and a second end coupled to a movable element, a knob coupled to the element, and means disposed in the handle portion for guiding the movement of the element and the knob. Furthermore, the guide means might include at least one elongated slot cooperating with one or more pins for coupling the element and the knob. The slot might further be configured to provide a means for applying a compressive force between at least two of the coupling members through the coaction of the pin and a curve disposed in one end of the slot. Additionally, the slot might further include one or more notches along the length of the slot for releasably locking one of the coupling members in a number of positions relative to the other coupling members. The core might be slidably disposed in a conduit located in the bore. Alternatively, the conduit might be slidably disposed in the core located in the bore.

In yet another contemplated form of the invention, the surgical instrument comprises an intermediate portion having a tubular member including a flexible conduit and a flexible core located within the tubular member. The tubular member might further be a position retaining flexible member capable of multiple planar orientation and further be capable of manipulation to achieve 360° spherical rotation.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there is illustrated and described typical embodiments of the invention.

BRIEF DESCRIPTION OF THE DRAWINGS

FIG. 1 is a schematic representation of a surgical instrument used for establishing compression anastomosis, in accordance with the principles of the present invention, illustrating a general overall view of the device.

FIG. 2 is an enlarged partial perspective view of the handle portion of the instrument depicted in FIG. 1 showing the aligning feature of the device locked in place rendering the driving feature operational.

FIG. 3 is a partial schematic representation of a surgical instrument like that of FIG. 1 showing the head portion of the device and a modified intermediate portion.

FIG. 3A is a view much like that depicted in FIG. 3 showing yet another modified intermediate portion.

FIG. 4 is an enlarged fragmented sectional view taken along the length of the instrument illustrated in FIG. 1, additionally including an uncoupled assembly, and showing the instrument and the assembly located in a colon but before assembly coupling and before the instrument is withdrawn from the patient leaving the assembly in place until the anastomosis has healed.

FIG. 5 is an enlarged partially sectioned view of the handle portion of the instrument shown in FIG. 4 and depicting the coupling member aligning feature in an operative mode while the driving feature is locked against movement, positioning the coupling members in an orientation like that represented in FIG. 12.

FIG. 6 is a view like that depicted in FIG. 5 but with the aligning feature in another position, the driving feature still being locked.

FIG. 7 is a view somewhat like that illustrated in FIG. 6 but with the aligning feature being locked against movement and the driving feature in a operative mode prior to activation, the coupling members of the assembly being in a position like that shown in FIG. 13.

FIG. 8 is a view substantially as shown in FIG. 7 but with the driving feature having been fully activated, the coupling members of the assembly being in a position like that shown in FIG. 15.

FIG. 9 is an enlarged cross-sectional view taken along line 9—9 through the head portion of the instrument illustrated in FIG. 1.

FIG. 10 is an exploded fragmentary perspective cutaway view of the head portion of the instrument, the outer housing having been removed, and including the coupling members of the assembly.

FIG. 11 is an elongated cross-sectional view solely of the housing which forms a recess at the head portion location of the instrument.

FIG. 12 is schematic sectional representation of the instrument, including members of the coupling assembly, being located in free ends of a sectioned colon but before the coupling members are moved into locking engagement.

FIG. 13 is a schematic sectional representation similar to that illustrated in FIG. 12 showing members of the assembly approximated but before locking and before a cutting element advances to cut through captured colonic tissue and to cut through a coupling member of the assembly.

FIG. 14 is similar to FIG. 13 but shows the coupling members fully locked and the initial rotational movement of the driver and the cutter as the cutter begins its passage through the tissue.

FIG. 17 is similar to FIG. 16 and illustrates that, after withdrawal of the instrument, the coupled assembly remains in the colon, which assembly will hold the captured colonic tissue in place until the anastomosis is healed and thereafter naturally be expelled intact by the patient.

DETAILED DESCRIPTION OF THE PREFERRED EMBODIMENTS

Figure 15:
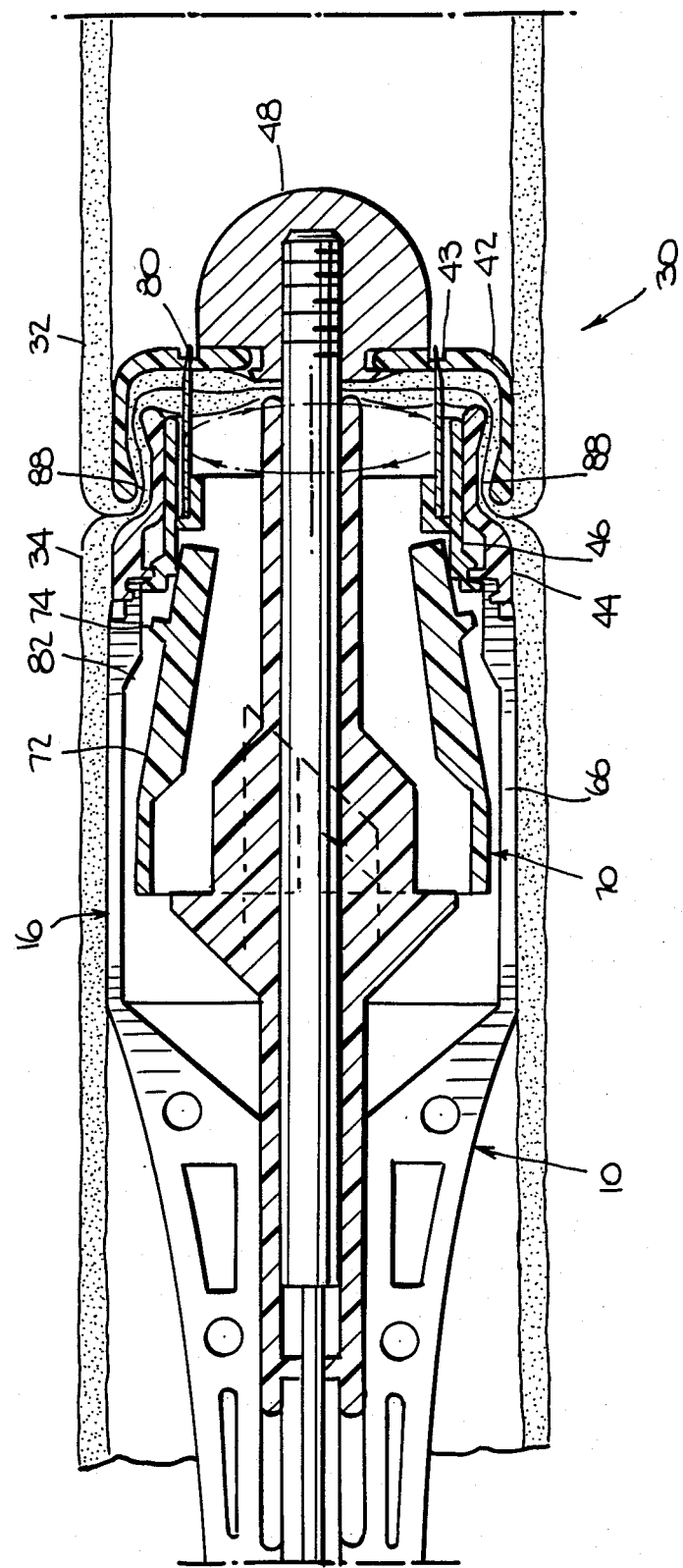
FIG. 15 is similar to FIG. 14 and shows further rotational movement of the driver and particularly illustrates the rotational movement imparted to the cutter as the cutter passes through both the tissue and the coupling member.

The description herein presented refers to the accompanying drawings in which like reference numerals refer to like parts throughout the several views. First turning to FIG. 1 there is illustrated a schematic representation of surgical instrument 10 of the present invention depicting a general overall view of the device. The instrument includes handle portion 12, intermediate portion 14 and head portion 16. Also shown on FIG. 1 and explained later in greater detail with respect to other drawing figures are knob 18, one of a pair of guide slots 20, safety locking element 22, lever 24, pivot pin 26 and core 28. Turning now to FIGS. 2, 3 and 3A, first there is illustrated in FIG. 2 an enlarged partial perspective view of handle portion 12 and in FIGS. 3 and 3A there is illustrated a partial schematic view showing head portion 16 and modified intermediate portions 14' and 14". Portion 14' is curved at an angle with respect to the center line of the handle portion. Portion 14" is a position retaining flexible member, like a gooseneck, which can assume a variety of orientations. Portion 14" is capable of multiple planar orientation and may be manipulated to achieve 360° spherical rotation. The intermediate portion 14 of FIG. 1 is substantially straight and horizontal whereas in intermediate portion 14' of FIG. 3 the angle $\alpha$ might range from about 10° to about 25° with the preferred angle $\alpha$ being about 15°. FIG. 4 depicts a fragmented sectional view of instrument 10, taken along the length of the instrument with a segment of intermediate portion 14 removed, showing the instrument located in colon 30 having wall portions 32, 34, and being used in conjunction with coupled assembly 40 including coupling members 42, 44 and 46 (46 not being shown in this view). Coupling member 42 is carried by core 28 and held thereon by end knob 48 coupled to core 28.

Now turning to FIGS. 5 through 8, there is best seen the operation of aligning, locking and driving features associated with the operation of instrument 10, which features are located in handle portion 12. Specifically, FIG. 5 depicts the aligning feature of instrument 10 in a first operative location positioning coupling member 42 of assembly 40 as shown in FIG. 12. The aligning feature comprises movable element 50 (located in handle portion 12) having recess 52 disposed therein and coupled at one end to core 28 and at the other end to knob 18 via pin 54. The movement of element 50 is guided within the handle by means of pin 54 traveling along slots 20 which have a curved portion 56 at one end of each slot. Each slot 20 might further include notches 21 for positioning element 50 at selected locations along the slot by locating pin 54 in the desired notch. Full operation of the aligning feature will be discussed in respect to FIGS. 6 and 7. FIG. 5 further depicts driving means 58 engaging end cap 60 of conduit 62. The end cap and conduit are slidably positioned in bore 63 running through intermediate portion 14 and intersecting a recess (FIG. 11) in head portion 16. Core 28, which might be either flexible or rigid, is slidably disposed in conduit 62, which also might be either flexible or rigid. A flexible conduit and a flexible core are preferred, particularly when intermediate portion 14 assumes a configuration other than straight. In an alternate construction, not shown, the conduit could be slidably disposed in the core. FIG. 5 shows locking element 22, in one position, locking driving means 58 against movement wherein at location 64 a portion of lever 24 rests against the top surface of locking element 22 thereby precluding lever 24 from pivoting about pin 26 and driving conduit 62 toward head portion 16. As can be seen in the perspective representation of FIG. 2, if element 22 were advanced toward head portion 16, downward projection 23 would abut the top surface of element 22 precluding downward movement of lever 24.

FIG. 6 is a view much like that of FIG. 5 but now shows the aligning feature in a second operative location. Knob 18, element 50 and core 28 have moved toward the left, advancing coupling member 42 into approximation with coupling member 44 much like that shown in FIG. 13. Lever 24 and driving means 58 remain locked against movement. The rotation of knob 18 and element 50, from the locked position (leftmost along handle 12) to any of a number of operating locations along slot 20, twists core 28 and sets up torsional forces in the core. The torsional or twisting forces set up in the core serve to urge pin 54 into a locked position when the pin is located within a slot 21. FIG. 7 is a view much like that of FIG. 6 but now shows the aligning feature in another location. Knob 18, element 50 and core 28 have been moved to their leftmost operating location wherein knob 18, pin 54 and element 50 have been rotated into the position shown. Pin 54 has traveled through curved portions 56 of slots 20 completing the approximation of coupling members 42, 44 establishing compression between members 42, 44 as is shown in FIG. 13. The arrows indicate the direction of movement of locking element 22 wherein downward force $P_1$ and rearward force $P_2$ are applied to 22 placing one end of 22 in recess 52 of element 50 thereby locking knob 18, element 50 and core 28 against movement. Element 50 is generally circular and fits snugly in circular handle portion 12 so that, with the introduction of an end of locking element 22 into recess 52, element 50 cannot be rotated thus locking knob 18, pin 54 and core 28 against movement. Although not shown, contemplated to be within the scope of the invention could be two locks that independently perform the dual locking functions of locking element 22. In the position shown, locking element 22 has been moved to allow for activation of lever 24 and driving means 58 since lever 24 is now free for rotation about pivot pin 26. However, in this view the lever and driving means have not been activated. FIG. 8 like FIG. 7 depicts locking element 22 in its leftmost position completely securing knob 18, core 28, element 50 and pin 54 against movement. With element 22 in this position, there is left an unobstructed pathway for the rotation of lever 24 about pivot 26 and the downward movement of projection 23 such that upon application of force F to lever 24 the lever rotates about pivot 26 causing driving means 58 to move end cap 60 and conduit 62 to the right. FIG. 8 depicts the driving means at rest after full activation. It should be understood that contemplated within the scope of the invention would be comparable driving means, namely, but not limited to, devices such as energy storing devices, threaded devices, slidable collars or rotating slidable collars.

Turning now to FIGS. 9 through 11, there are shown details of the head portion of the instrument. Specifically, FIG. 9 is an enlarged cross-sectional view of head portion 16 including outer housing 66 having recess 68, with driver 70 and core 28 located in recess or cavity 68. Additionally shown in FIG. 9 is that driver 70 includes tab 72 with projecting rib 74 and that tab 72 is positioned in guide channel 76 disposed in recess 68. In FIG. 10, there is shown an exploded fragmentary perspective cutaway view of head portion 10 with outer housing 66 removed. FIG. 10 specifically depicts driver support 69, driver 70 with tab 72, rib 74 and ledge 75 and further including angled projection 78 near the base of the driver. Furthermore there are shown cutter 80 and coupling members 42, 44 and 46 with member 42 further including recess 43. FIG. 11 depicts a cross-sectional view of housing 66 and includes channel 76 having a sloping end portion 82, ramp 84 and groove 86. In assembly for operation, coupling member 44 is carried by housing 66 as the end of member 44 snaps into the housing at location of annular groove 86; coupling member 46 rests on the end portion of tabs 72; and cutter 80 rests on driver ledge 75. Linear movement of driver 70 within recess 68 is guided by the location of tabs 72 in channels 76 and rotational movement of the driver and cutter 80 is caused by the gliding coaction of angled projection 78 as it rides along sloping ramp 84.

Figure 16:
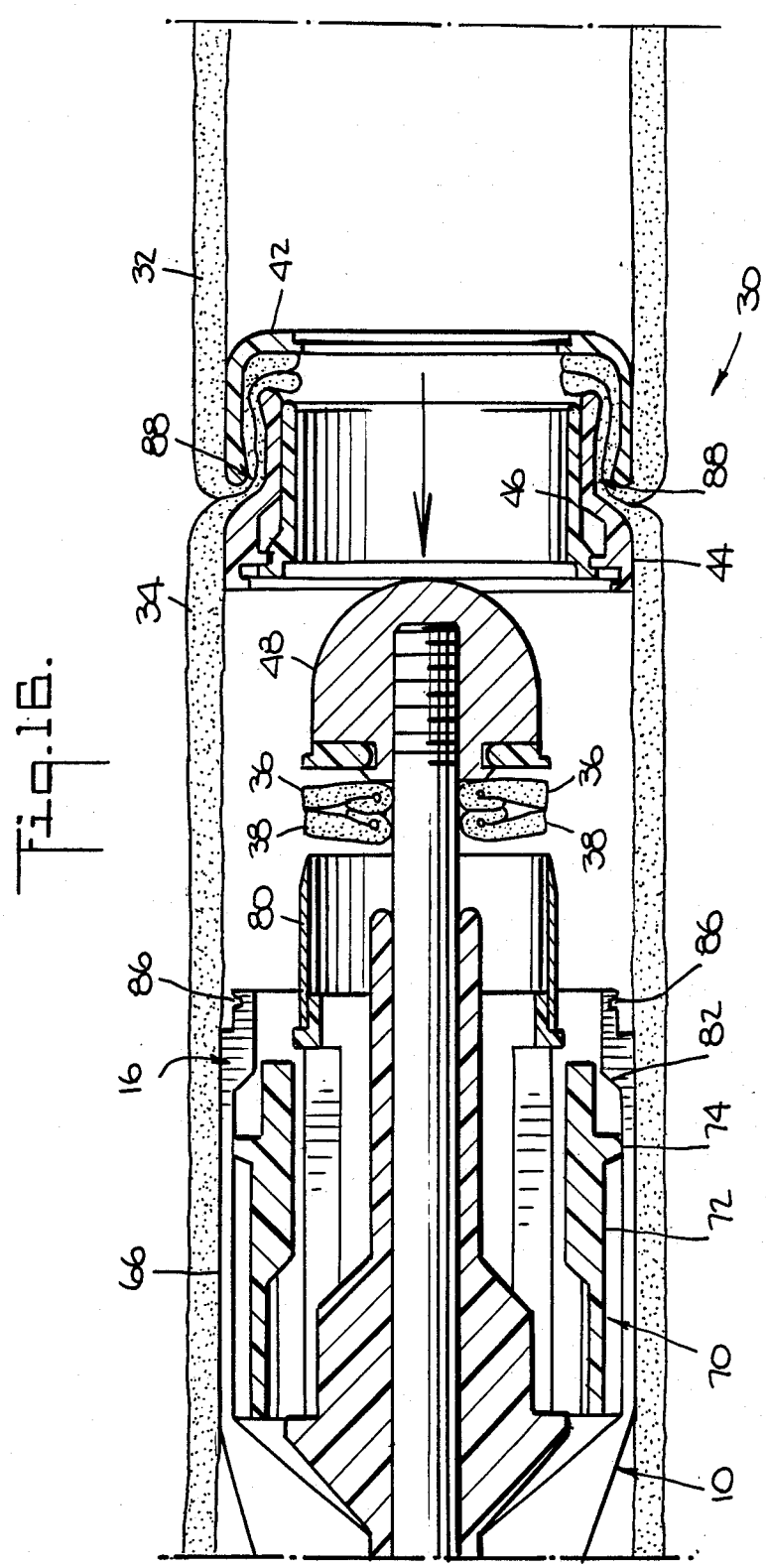
FIG. 16 is similar to FIG. 15 and shows the withdrawal of the instrument from the colon in the direction indicated.

Let us now turn to FIGS. 12 through 17 where there are shown a series of schematic views depicting the operation of the surgical instrument. FIG. 12 shows instrument 10 and coupling members 42, 44, 46 located in colon 30. While herein illustrated and described is the use of the instrument and coupling members in conjunction with colon repair, it should be understood that use thereof is equally applicable for the repair of other tubular organs such as the large and small bowel and the esophagus to name but a few. Here, colon 30 having wall portions 32, 34 and free ends 36, 38 is shown with the free ends being gathered against core 28. Coupling member 42 supported by core 28 and end knob 48 is located in one end of colon 30 while head portion 16 is located in the other end of the colon. Coupling member 42 is ready to be moved into approximation with member 44. FIG. 13 shows the coupling members approximated, core 28 having been moved to the left to bring ends 36, 38 into contact, but before locking of the members and before tissue and coupling member cutting. Compression of tissue between members 42, 44 is achieved by the movement of knob 18 and pin 54 through curved portion 56 at the handle end of the instrument and member 42 is secured against movement by locking the aligning means in a manner heretofore specified. The coupling members are now ready for locking and cutting by the operation of driving means 58 and driver 70 wherein the driving means will urge the driver forward. FIGS. 14 and 15 depict further operation of the instrument. Driver 70 rests in channels 76 of housing 66 and the coacting configuration of the inner housing and driver glides the movement of the driver when the driving means is activated. Specifically, driver 70 has tabs 72 and angled projections 78 with the tabs 72 being positioned in channels 76 and angled projections 78 contacting sloping ramp surface 84. The driver is adapted to first move linearly forward as tabs 72 advance in channels 76 and then to rotate as angled projections 78 ride along ramp surface 84. Tabs 72 push coupling member 46 forward until it snaps into coupling member 44, thus locking together coupling members 42, 44 and 46. Thereafter, tabs 72, which are flexible, bend inwardly as rib 74 of each tab rides along sloping surface 82 at the end of channel 76, gradually decreasing the inner diameter of the channel that the tab rides in, and the tabs move inside coupling member 46. Attached to driver 70 is cutter 80 which cuts excess tissue, namely, free colon ends 36, 38, and through cut ring or recess 43 located in coupling member 42. When tabs 72 fold inwardly, driver 70 is free to move further forward without moving the coupled members of the assembly. The driver moves forward, rotating as it advances, and imparts a rotary motion to cutter 80 which cuts through the tissue and the coupling member. The rotation of cutter 80 facilitates the smooth cutting action necessary to cut the tissue and the coupling member, clearing the lumen and allowing for the detachment of the instrument from the assembly. Rib 74 bumps an end of member 46 pushing member 46 and coupled member 44 dislodging member 44 from its attachment to housing 66 at groove 86 and freeing the coupled assembly from instrument 10. FIG. 16 shows the withdrawal of instrument 10 from the colon leaving the coupled assembly at the anastomosis site as shown in FIG. 17. The anastomosis will heal in and about the region designated 88 and thereafter the assembly will naturally be expelled intact by the patient leaving colon 30, at the anastomotic site, with an open, unobstructed passageway substantially like that which existed before resectioning.

While in accordance with provisions of the statutes there is described herein specific embodiments of the invention, those skilled in the art will understand that changes may be made in the form of the invention covered by the claims appended hereto without departing from the scope and spirit thereof, and that certain features of the invention may sometimes be used to an advantage without corresponding use of the other features.

We claim:

1. A device for installing a coupling assembly having a plurality of coupling members for compression anastomosis of a tubular structure comprising a body having a bore and including driver means and cutter means, means for imparting rotational movement to said cutter means, means for supporting the coupling members of said assembly, means for aligning said coupling members and means for driving said driver means for urging said coupling members into locking engagement and advancing and rotating said cutter means.

2. A device for installing a coupling assembly having a plurality of coupling members for compression anastomosis of a tubular structure comprising
   a body having a bore located therein and including a handle portion, an intermediate portion and a head portion, with said head portion having a recess intersecting said bore;
   said recess being dimensioned and configured to include therein driver means and cutter means;
   means for imparting rotational movement to said cutter means;
   means for supporting the coupling members of said assembly;
   means for aligning said coupling members; and
   means for driving said driver means for urging said coupling members into locking engagement and advancing and rotating said cutter means.

3. The device according to claim 2 wherein said recess includes means for guiding the movement of said driver means.

4. The device according to claim 3 wherein said guiding means includes at least one channel disposed in said recess, with said channel slidingly engaging at least one tab disposed on said driver means.

5. The device according to claim 4 wherein said tab further includes means for disengaging said device from said assembly after assembly installation.

6. The device according to claim 5 wherein said disengaging means comprises at least one rib disposed on said tab.

7. The device according to claim 2 wherein said rotational means comprises ramp means for engaging and guiding complementary projecting means.

8. The device according to claim 7 wherein said ramp means includes at least one angled surface disposed in said recess and said projecting means includes at least one land disposed on said driver means, with said angled surface and said land being designed and configured for gliding coaction.

9. The device according to claim 7 wherein said ramp means includes at least one angled surface disposed on said driver means and said projecting means includes at least one land disposed in said recess, with said angled surface and said land being designed and configured for gliding coaction.

10. The device according to claim 2 further including one or more locking means for alternately locking said driving means and said aligning means against movement.

11. The device according to claim 10 wherein said locking means is adapted for movement between first and second locking positions.

12. The device according to claim 11 wherein said locking means in a first position releasably locks said driving means against movement while simultaneously allowing operation of said aligning means, said driving means being inoperative while said aligning means is operational.

13. The device according to claim 11 wherein said locking means in a second position releasably locks said aligning means against movement while simultaneously allowing operation of said driving means, said aligning means being inoperative while said driving means is operational.

14. The device according to claim 2 wherein said driving means includes a conduit slidably disposed in said bore, a first end of said conduit being adapted to engage a lever and a second end of said conduit being adapted to engage said driver means.

15. The device according to claim 2 wherein said aligning means comprises a core having a first end coupled to one of said coupling members and a second end coupled to a movable element, a knob coupled to said element, and means disposed in said handle portion for guiding the movement of said element and said knob.

16. The device according to claim 15 wherein said guide means includes at least one elongated slot cooperating with at least one pin coupling said element and said knob adapted for positioning said one coupling member relative to the other said coupling members.

17. The device according to claim 16 wherein said guide means further includes means for applying a compressive force between at least two of said coupling members.

18. The device according to claim 17 wherein said compressive force is achieved through a coaction of said pin and a curve disposed in one end of said slot.

19. The device according to claim 18 wherein said slot further includes one or more notches disposed along said slot for releasably locking said one coupling member in one or more positions relative to the other said coupling members.

20. The device according to claim 15 wherein said core is slidably disposed in a conduit disposed in said bore.

21. The device according to claim 20 wherein said conduit is slidably disposed in said core.

22. The device according to claim 2 wherein said intermediate portion is substantially straight.

23. A device for installing a coupling assembly having a plurality of coupling members for compression anastomosis of a tubular structure comprising
a body having a bore located therein and including a handle portion, an intermediate portion and a head portion, with said head portion having a recess intersecting said bore;
said recess being dimensioned and configured to include therein driver means and cutter means;
means for supporting the coupling members of said assembly;
means for aligning said coupling members;
means for driving said driver means for urging said coupling members into locking engagement and advancing said cutter means; and
locking means for alternately locking said driving means and said aligning means.

24. The device according to claim 23 wherein said locking means is adapted for movement between first and second locking positions.

25. The device according to claim 24 wherein said locking means in a first position releasably locks said driving means against movement while simultaneously allowing operation of said aligning means, said driving means being inoperative while said aligning means is operational.

26. The device according to claim 24 wherein said locking means in a second position releasably locks said aligning means against movement while simultaneously allowing operation of said driving means, said aligning means being inoperative while said driving means is operational.

27. A device for installing a coupling assembly having a plurality of coupling members for compression anastomosis of a tubular structure comprising
a body having a bore located therein and including a handle portion, an intermediate portion and a head portion, with said head portion having a recess intersecting said bore;
said recess being dimensioned and configured to include therein driver means and cutter means;
means for supporting the coupling members of said assembly;
means for aligning said coupling members, said aligning means comprising a core having a first end coupled to one of said coupling members and a second end coupled to a movable element, a knob coupled to said element, and guiding means disposed in said handle portion for directing the movement of said element and said knob for positioning said one coupling member relative to other said coupling members, with said guiding means including at least one elongated slot cooperating with at least one pin coupling said element and said knob for slidable conjoint axial movement; and
means for driving said driver means for urging said coupling members into locking engagement and advancing said cutter means.

28. The device according to claim 27 wherein said guiding means further includes means for applying a compressive force between at least two of said coupling members.

29. A device for installing a coupling assembly having a plurality of coupling members for compression anastomosis of a tubular structure comprising
a body having a bore located therein and including a handle portion, an intermediate portion and a head portion, with said head portion having a recess intersecting said bore;
said recess being dimensioned and configured to include therein driver means and cutter means;
means for supporting the coupling members of said assembly;
means for aligning said coupling members, said aligning means comprising a core having a first end coupled to one of said coupling members and a second end coupled to a movable element, a knob coupled to said element, and guiding means disposed in said handle portion for directing the movement of said element and said knob positioning said one coupling member relative to the other said coupling members, with said guiding means including at least one elongated slot cooperating with at least one pin coupling said element and said knob and further including means for applying a compressive force between at least two of said coupling members through a coaction of said pin and a curve disposed in one end of said slot; and
means for driving said driver means for urging said coupling members into locking engagement and advancing said cutter means.

30. A device for installing a coupling assembly having a plurality of coupling members for compression anastomosis of a tubular structure comprising
a body having a bore located therein and including a handle portion, an intermediate portion and a head portion, with said head portion having a recess intersecting said bore;
said recess being dimensioned and configured to include therein driver means and cutter means;
means for supporting the coupling members of said assembly;
means for aligning said coupling members, said aligning means comprising a core having a first end coupled to one of said coupling members and a second end coupled to a movable element, a knob coupled to said element, and guiding means disposed in said handle portion for directing the movement of said element and said knob positioning said one coupling member relative to the other said coupling members, with said guiding means including at least one elongated slot cooperating with at least one pin coupling said element and said knob, and with said slot further including one or more notches disposed along said slot for releasably locking said one coupling member in one or more positions relative to the other said coupling members; and
said for driving said driver means for urging said coupling members in locking engagement and advancing said cutter means.

31. A device for installing a coupling assembly having a plurality of coupling members for compression anastomosis of a tubular structure comprising
a body having a bore located therein and including a handle portion, an intermediate portion and a head portion, with said head portion having a recess intersecting said bore;
said recess being dimensioned and configured to include therein driver means and cutter means;
means for supporting the coupling members of said assembly;
means for aligning said coupling members;
means for driving said driver means for urging said coupling members into locking engagement and advancing said cutter means; and
locking means for releasably locking said aligning means against movement.

* * * * *